United States Patent [19]

Gersdorf et al.

[11] Patent Number: 4,977,066
[45] Date of Patent: Dec. 11, 1990

[54] ALKENYLPHOSPHONIC AND -PHOSPHINIC ACID ESTERS, PROCESS FOR THEIR PREPARATION, AND A RADIATION-POLYMERIZABLE MIXTURE CONTAINING SAID COMPOUNDS

[75] Inventors: Joachim Gersdorf, Wiesbaden; Hans-Jerg Kleiner, Kronberg, both of Fed. Rep. of Germany

[73] Assignee: Hoechst Aktiengesellschaft, Frankfurt am Main, Fed. Rep. of Germany

[21] Appl. No.: 354,730

[22] Filed: May 22, 1989

[30] Foreign Application Priority Data

May 21, 1988 [DE] Fed. Rep. of Germany ....... 3817424

[51] Int. Cl.$^5$ .................... G03F 7/027; G03C 1/77
[52] U.S. Cl. .................... 430/277; 430/278; 430/279; 430/275; 430/273; 430/271; 430/281; 430/288; 522/115; 522/141; 522/142; 522/171; 525/340; 526/275; 558/86; 558/161; 558/177
[58] Field of Search ............... 522/115, 141, 142, 171; 525/340; 430/271, 273, 275, 277, 278, 279, 281, 288; 558/86, 161, 177

[56] References Cited

U.S. PATENT DOCUMENTS

| | | | |
|---|---|---|---|
| 2,892,716 | 6/1959 | Martin | 96/115 |
| 3,179,518 | 4/1965 | Sus et al. | 96/33 |
| 3,197,308 | 7/1965 | Stahlhofen | 96/33 |
| 3,206,474 | 9/1965 | Hechenbleikner et al. | 558/177 |
| 3,297,663 | 1/1967 | Herbst et al. | 260/80 |
| 3,349,150 | 10/1967 | Hechenbleikner et al. | 558/177 |
| 3,957,918 | 5/1976 | Dickie et al. | 522/115 |
| 3,987,127 | 10/1976 | Dickie et al. | 522/115 |
| 4,264,658 | 4/1981 | Tobias et al. | 522/115 |
| 4,276,234 | 6/1981 | Honig et al. | 558/177 |

FOREIGN PATENT DOCUMENTS 1302833 3/1971 Fed. Rep. of Germany.

OTHER PUBLICATIONS

Chemical Abstracts, Synthetic High Polymers, vol. 96, No. 26, Jun. 28, 1982, p. 3, 218261q.
Chemical Abstracts, Synthetic High Polymers, vol. 78, No. 14, Apr. 9, 1973, p. 5, 84877n.

Primary Examiner—Marion C. McCamish
Assistant Examiner—Christopher D. RoDee
Attorney, Agent, or Firm—Foley & Lardner, Schwartz, Jeffery, Schwaab, Mack, Blumenthal & Evans

[57] ABSTRACT

Esters of trihydric or tetrahydric alcohols with alkenylphosphonic or -phosphinic acids, which can be polymerized by means of actinic light, are disclosed. They are combined with polymeric binders, in particular water-soluble polymers, and free-radical-forming photoinitiators to form photopolymerizable mixtures which are suitable for the preparation of photoresists and the production of printing plates. The mixtures show reduced temperature sensitivity and have long shelf lives.

9 Claims, No Drawings

ALKENYLPHOSPHONIC AND -PHOSPHINIC ACID ESTERS, PROCESS FOR THEIR PREPARATION, AND A RADIATION-POLYMERIZABLE MIXTURE CONTAINING SAID COMPOUNDS

BACKGROUND OF THE INVENTION

This invention relates to alkenyl phosphonic and -phosphinic acid esters of certain polyhydric alkanols, a process for their preparation, and radiation-polymerizable mixtures containing these esters as polymerizable compounds.

Esters and other derivatives of alkenyl phosphonic and -phosphinic acids with usually monohydric alcohols are known and are employed on a large industrial scale for the preparation of polymers, for example of polyvinylphosphonic acid and its derivatives. Direct utilization of the unsaturated compounds mentioned—apart from the preparation of polymers—has hitherto only been carried out to a small extent, virtually only the acidic properties of the monomers being used without the polymerizability of the alkenyl group being utilized. This is presumably attributable to the relatively low tendency towards polymerization of the known alkenyl phosphonic acids or their derivatives, which is mentioned in DE-C No. 1,106,963.

Photopolymerizable mixtures for the production of printing plates and for the preparation of photoresists and other photosensitive materials contain compounds which can be polymerized by the action of actinic light, in the presence of a photoinitiator to form cross-linked, insoluble products. Compounds of this type which have been employed hitherto are virtually exclusively esters of unsaturated carboxylic acids, in particular of acrylic acid and methacrylic acid, with polyhydric aliphatic or cycloaliphatic alcohols, which may optionally contain urethane or ether groups. In earlier publications, for example in U.S. Pat. No. 2,892,716, divinyl esters of aromatic or aliphatic disulfonic acids are mentioned as polymerizable compounds, but these have not been introduced into practice.

The (meth)acrylates of polyhydric alcohols which have been preferred hitherto have certain disadvantages, at least for some applications. They are unstable at elevated temperatures, for example above 150° C.; in addition, many low-molecular-weight representatives have high volatility, which becomes noticeable on relatively long storage in the coating and on processing at elevated temperatures. In addition, most of the preferred representatives are water-insoluble and thus rather difficult to combine with water-soluble or hydrophilic binders. Additionally, most (meth)acrylates cause harmful skin irritations.

SUMMARY OF THE INVENTION

Accordingly, it is an object of the present invention to provide an improved radiation-polymerizable compound.

Another object of the present invention is to provide a radiation-polymerizable compound, the polymerizability of which on irradiation in the presence of radiation-activatable initiators, such as photoinitiators, is comparable to that of presently known acrylates or methacrylates.

A further object of the present invention is to provide a radiation-polymerizable compound which is water-soluble, less volatile and less irritating to the skin than presently known acrylates or methacrylates.

In accomplishing the foregoing objectives, there has been provided, in accordance with one aspect of the present invention, a compound of the general formula I

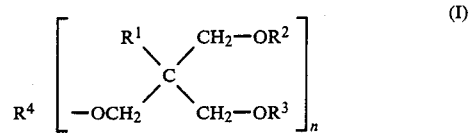

in which
R$^1$ denotes an alkyl group having 1 to 4 carbon atoms, CH$_2$OH or CH$_2$OR$^7$,
R$^2$ denotes group of the formula II

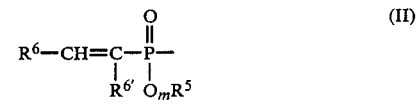

R$^3$ denotes a hydrogen atom or a group of the formula II, or in which
R$^2$ and R$^3$ together denote a group of the formula III

n is 1 or 2,
R$^4$, in the case where n=1, denotes a hydrogen atom, a group of the formula II, or, if R$^2$ and R$^3$ form a group of the formula III and R$^1$ is an alkyl group, alternatively denotes a group of the formula IV

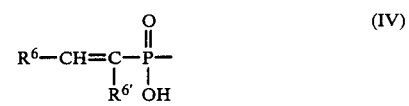

or, together with R$^7$, denotes a group of the formula III, and, in the case where n=2, denotes a group of the formula III,
R$^5$ denotes an alkyl group having 1 to 4 carbon atoms,
R$^6$ and R$^{6'}$ are identical or different and each denotes a hydrogen atom or an alkyl group having 1 to 4 carbon atoms,
R$^7$ denotes a group of the formula II, and
m is 0 or 1.

In accordance with another aspect of the present invention, there is provided a process for the preparation of the compounds of the formula I which comprises the step of reacting an alkenylphosphonic acid compound of the formula V

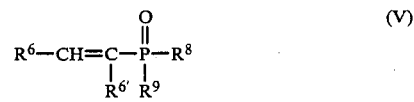

or an alkenyl phosphinic acid compound of the formula VI

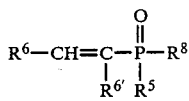

in which
R[8] and R[9] are identical or different and each denotes a halogen atom, an OH group or an alkoxy group having 1 to 4 carbon atoms, and
R[5], R[6] and
R[6'] have the above-mentioned meaning, with a trihydric or tetrahydric alcohol of the formula VII

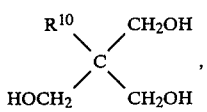

in which
R[10] denotes an alkyl group having 1 to 4 carbon atoms or a CH$_2$OH group.

The compounds according to the invention are used as polymerizable compounds in mixtures which can be polymerized by radiation, in particular by visible or ultra-violet light.

In accordance with a further aspect of the present invention, there is provided a radiation-polymerizable mixture which comprises
(a) a polymeric binder,
(b) a compound which can be polymerized by means of free radicals, and
(c) a compound or a compound combination which is capable of initiating polymerization of the compound (b) under the action of actinic radiation.

In the mixture according to the invention, the polymerizable compound is a compound of the abovementioned general formula I.

Furthermore according to the invention, a radiation-polymerizable recording material having a radiation-sensitive layer and optionally a layer support is provided in which the radiation-sensitive layer comprises a mixture of the above-mentioned composition.

Other objects, features and advantages of the present invention will become apparent to those skilled in the art from the following detailed description. It should be understood, however, that the detailed description and specific examples, while indicating preferred embodiments of the present invention, are given by way of illustration and not limitation. Many changes and modifications within the scope of the present invention may be made without departing from the spirit thereof, and the invention includes all such modifications.

DETAILED DESCRIPTION OF PREFERRED EMBODIMENTS

According to an embodiment of the process, an alkenylphosphonic acid halide of the formula V where R[8]=R[9]=halogen, preferably chlorine, is reacted in the presence of a tertiary amine in the molar ratio 1:2:1 in a suitable inert solvent with a 1,1,1-trishydroxymethylalkane. Examples of tertiary amines which can be employed are triethylamine, N,N'-dimethylaniline or pyridine. Examples of suitable solvents are methylene chloride, toluene, acetonitrile or tetrahydrofuran. The reactions are preferably carried out with cooling at −10° to +40° C. For example, the compounds 1 and 2 of Table I surprisingly are obtained here in very good yields.

According to another embodiment, an alkenylphosphinic acid halide of the formula VI where R[8]=halogen, for example methylvinylphosphinic acid chloride, is reacted with a 1,1,1-trishydroxymethylalkane or pentaerythritol in the presence of a tertiary amine to form a compound of the formula I where R[1]=alkyl or CH$_2$OR[7]. In this way, the compound 7 is obtained.

According to a further variant, alkenyl phosphonic acid halide esters can be employed in accordance with this process, for example the compound 8 is obtained from 3 moles of ethyl vinylchlorophosphonate, 3 moles of tertiary amine and 1 mole of 1,1,1-trimethylolpropane.

The products produced, which still contain free hydroxyl groups, can be reacted further, for example with alkenyl phosphonic anhydrides, such as vinyl phosphonic anhydride. This reaction is carried out in an inert solvent, for example methylene chloride or dimethylformamide. In this way, the compound 3 is obtained from 1 mole of a vinylphosphonic anhydride unit and 1 mole of compound 2.

It is furthermore possible to react compounds according to the invention which contain free OH groups, for example the compounds 1, 2 or 6, with alkenylphosphinic acid halides or alkenylphosphonic acid halide esters. In this case, for example, the compounds 4 and 5 are obtained.

It is also possible to react alkenylphosphonic acid dichlorides with, for example, the compounds 1, 2 or 6. In this case, for example, the compound 9 is obtained from compound 2.

According to another embodiment of the process, alkenylphosphonic acids or alkenylphosphinic acids are esterified using polyhydric alcohols of the formula VII. In this case, the acids and the particular alcohol are mixed in the desired stoichiometric ratio in each case and then kept at 150° to 250° C., preferably 160° to 220° C., in a suitable vacuum, during which esterification takes place with elimination of water. It may be expedient to add certain known polymerization inhibitors, for example hydroquinone, hydroquinone monomethyl ether or phenothiazine. It may furthermore be advantageous not to carry out the esterification to completion, but instead to terminate it at a certain residual acid content, since otherwise the reaction duration must be extended excessively and polymerization of the reaction products cannot always be prevented under these conditions. For example, the compounds 2 and 7 are obtained by esterification of vinylphosphonic acid or vinylmethylphosphinic acid using 1,1,1-trimethylolpropane.

Finally, alkenylphosphonic and -phosphinic acid esters can be transesterified using alcohols of the formula VII in the presence of suitable catalysts. Examples of catalysts which can be employed are alkali metal alcoholates or alkali metal hydrides, for example sodium hydride, but also tetraisopropyl orthotitanate. The transesterification reaction is preferably carried out in vacuo in the temperature range 150° to 250° C., in particular 180° to 220° C. For example, the compound 7 is obtained by this procedure from 3 moles of ethyl vinylmethylphosphinate and mole of trimethylolpropane.

The alkenylphosphonic and -phosphinic acid esters produced in the process indicated can be purified by distillation in a high vacuum, in particular using a thin-film evaporator. They can in some cases also be employed directly as a crude product without further purification.

In the general formula I, $R^1$, if an alkyl radical, preferably has 1 or 2 carbon atoms. $R^5$ preferably has 1 to 3 carbon atoms, and $R^6$ is preferably a methyl group or a hydrogen atom, in particular a hydrogen atom.

An essential advantage of the compounds according to the invention is their very good solubility both in polar and in non-polar solvents. Thus, the compounds according to the invention, in contrast to trimethylolpropane triacrylate and trimethylolpropane trimethacrylate, are miscible in any ratio with water. The compounds according to the invention are low-volatility, low-odour substances. This gives the further advantage of the significantly reduced tendency towards diffusion or evaporation from photopolymerizable coatings. They are furthermore distinguished by a significantly higher thermostability than the customary acrylates and methacrylates.

The proportion of monomers in the coating is generally about 5 to 80% by weight, preferably 8 to 60%.

Binders which can be used are a large number of soluble organic polymers. Examples which may be mentioned are: polyamides, polyvinyl esters, polyvinyl acetals, epoxy resins, polyacrylates, polymethylacrylates, polyesters, alkyd resins, polybutadiene, polyisoprene, isoprenestyrene block copolymers and other elastomers, and copolymers of the monomers which form the homopolymers listed.

It is also possible to use binders which are insoluble in water, but soluble or at least swellable in aqueous-alkaline solutions, since coatings containing such binders can be developed using aqueous-alkaline developers. Binders of this type can contain, for example, the following groups: —COOH, —$PO_3H_2$, —$SO_3H$; —$SO_2NH$—, —$SO_2$—NH—$SO_2$— and —$SO_2$—NH—CO—.

Examples which may be mentioned as such binders are: maleic resins, polymers made from β-(methacryloyloxy)ethyl N-(p-tolylsulfonyl)-carbamate and copolymers of these and similar monomers with other monomers, vinyl acetate/crotonic acid, styrene/maleic anhydride, alkyl methacrylate/methacrylic acid copolymers and copolymers made from methacrylic acid, higher alkyl methacrylates and methylmethacrylate and/or styrene or acrylonitrile.

It is particularly advantageous to use mixtures based on water-soluble binders since the water-soluble polymerizable compounds according to the invention can be combined therewith particular easily and allow easy and environmentally friendly coating from aqueous solution. Examples of such binders are polyvinyl alcohol, partially hydrolysed polyvinyl acetates and vinyl acetate copolymers, polyvinyl ethers, polyvinylpyrrolidone, polyacrylamide, polydimethylacrylamide, polyethylene oxide, polyvinylmethylformamide, polyvinylmethylacetamide and water-soluble natural polymers.

The amount of binder is generally about 20 to 95% by weight of the components of the coating, preferably 40 to 90%.

The photopolymerizable mixtures can contain various substances as additives, depending on the planned application and depending on the desired properties. Examples are: polymerization inhibitors, hydrogen donors, dyes, colored and non-colored pigments and plasticizers.

In the context of this description, actinic radiation is to be understood as being any radiation whose energy corresponds at least to that of visible light. For example, visible light, long-wave and short-wave UV radiation, laser radiation, electron radiation and X-ray radiation are suitable.

A large number of substances can be used as photoinitiators in the mixture according to the invention. Examples are those which are derived from the benzophenone, acetophenone, benzoin, benzil, benzil monoketal, fluorenone, thioxanthone, polynuclear quinone, acridine and quinoxaline basic structure; furthermore trichloromethyl-s-triazines, 2-halomethyl-5-vinyl-1,3,4-oxadiazole derivatives, trichloromethyl-substituted halooxazoles, trihalomethyl-containing carbonylmethylene heterocycles as per DE-A No. 3,333,450, or acylphosphine oxide compounds, as described, for example, in DE-A No. 3,133,419, are suitable.

The initiators are generally employed in an amount of from about 0.01 to 10% by weight, preferably from 0.05 to 4% by weight, based on the non-volatile components of the mixture.

If the image formation is to be carried out using X-rays or electron beams, suitable photoiniators, besides the known photoinitiators which are sensitive to visible and near UV light, are also those whose absorption regions are in the short-wave part of the electromagnetic spectrum and which are thus fairly insensitive to daylight. This has the advantage that the recording materials can be handled without exclusion of light and that the materials car be imparted with a better shelf life. The examples which may be mentioned as such initiators are tribromomethyl phenyl sulfone, 2,2',4,4',6,6'-hexabromodiphenylamine, pentabromoethane, 2,3,4,5-tetrachloroaniline, pentaerythritol tetrabromide, chloroterphenyl resins or chlorinated paraffins.

The photopolymerizable mixture can be employed for a wide variety of applications, for example for the production of surface coating materials which are cured by the action of light, as dental filling or replacement material and, in particular, as photosensitive recording material in the field of reproduction.

The detailed description of the invention is limited to this last-mentioned area of application, but the invention is not limited thereto. Possible applications in this area which may be mentioned are: recording layers for the photomechanical production of printing plates for letterpress printing, particularly flexographic printing, planographic printing, rotogravure printing and screen printing, of relief copies, for example the production of texts in braille, of individual copies, tanned images, pigmented images, etc. Furthermore, the mixtures can be used for the photomechanical preparation of etch resists, for example for the manufacture of name plates, of copied circuits and for chemical milling. The mixtures according to the invention are particularly important as copying layers for the photomechanical production of printing plates and for photoresist technology.

The commercial utilization of the mixture for the applications mentioned can take place in the form of a liquid solution or dispersion, for example as a photoresist solution, which is applied to the individual layer supports by the user himself, for example for chemical milling, for the production of copied circuits, of screen printing screens and the like. As a solid, photosensitive layer on a suitable support, the mixture can also be in the form of a storable, precoated, photosensitive copying material, for example for the production of printing plates. It is also suitable for the preparation of dry resist.

It is generally favorable to substantially prevent exposure of the mixtures to atmospheric oxygen during photopolymerization. In the case of application of the mixture in the form of thin copying layers, it is advisable to apply a suitable, oxygen-impermeable covering film which can be removed mechanically or is soluble in the developer.

Suitable layer supports for the copying materials prepared using the mixture according to the invention are, for example, aluminum, steel, zinc, copper foils and plastic films, for example made from polyethylene terephthalate or cellulose acetate, and screen-printing substrates, such as Perlon gauze. It is in many cases favorable to subject the substrate surface to pre-treatment (chemical or mechanical) with the aim of properly adjusting the adhesion of the layer or reducing the reflectivity of the support in the actinic region of the copying layer (halation prevention).

The preparation of the photosensitive materials using the mixture according to the invention is carried out in a known manner. Thus, the mixture can be taken up in a solvent, and the solution or dispersion can be applied to the intended support by flow coating, spraying, dipping, roller application, etc., and subsequently dried. Thick layers (for example of 250 μm and greater) are advantageously produced by extrusion or pressing as a self-supporting film, which is then optionally laminated onto a support. In the case of dry resist, solutions of the mixture are applied to transparent supports and dried. The photosensitive layers, having thicknesses of between about 10 and 100 μm, are then in the same way laminated onto the desired final support , together with the temporary support.

The materials are processed in a known manner. Heating after exposure can be carried out to produce better crosslinking of the layer. For development, they are treated with a suitable developer liquid, for example with organic solvents, with slightly alkaline aqueous solutions or advantageously with water alone, the unexposed areas of the layer being removed and the exposed areas of the copying layer remaining on the substrate.

Working examples of the invention are indicated below. In these, percentages and amounts are to be understood as weight units, unless otherwise stated. First, the synthesis of some compounds according to the invention is described in a number of preparation examples. These and other compounds prepared according to the invention are indicated in Table I below. The preparation examples are followed by some use examples, which describe the use of the polymerizable compounds in the photopolymerizable recording materials.

TABLE 1

(Compounds of the formula 1)

| Compound No. | $R^1$ | $R^4$ | $R^2$ | $R^3$ | n |
|---|---|---|---|---|---|
| 1 | $CH_3$ | H | $\begin{array}{c}\diagdown\\ \diagup\end{array}\!\!\!P(=O)-CH=CH_2$ | | 1 |
| 2 | $C_2H_5$ | " | " | | " |
| 3 | " | $HO-P(=O)-CH=CH_2$ | " | | " |
| 4 | " | $CH_3-P(=O)-CH=CH_2$ | " | | " |
| 5 | " | $C_2H_5O-P(=O)-CH=CH_2$ | " | | " |
| 6 | " | H | $CH_3-P(=O)-CH=CH_2$ | $CH_3-P(=O)-CH=CH_2$ | " |
| 7 | " | $CH_3-P(=O)-CH=CH_2$ | " | " | " |
| 8 | " | $C_2H_5O-P(=O)-CH=CH_2$ | $C_2H_5O-P(=O)-CH=CH_2$ | $C_2H_5O-P(=O)-CH=CH_2$ | " |
| 9 | " | $\begin{array}{c}\diagdown\\ \diagup\end{array}\!\!\!P(=O)-CH=CH_2$ | $\begin{array}{c}\diagdown\\ \diagup\end{array}\!\!\!P(=O)-CH=CH_2$ | | 2 |

TABLE 1-continued (Compounds of the formula 1)

| Compound No. | R$^1$ | R$^4$ | R$^2$ | R$^3$ | n |
|---|---|---|---|---|---|
| 10 | | $\begin{array}{c}\diagdown\\ \diagup\end{array}\!\!\!\begin{array}{c}P-CH=CH_2\\ \|\\ O\end{array}$ | " | | 1 |
| 11 | —CH$_2$O—R$^7$ | | $R^2 = R^3 = R^4 = R^7 = CH_3-\underset{\underset{O}{\|}}{P}-CH=CH_2$ | | " |

PREPARATION EXAMPLES

Example 1 (Compound 1)

Reaction of vinylphosphonic acid dichloride with 1,1,1-trishydroxymethylethane.

240 g (2.0 mol) of 1,1,1-trishydroxymethylethane were combined with 404 g (4.0 mol) of triethylamine in 1,600 ml of tetrahydrofuran. 290 g (2.0 mol) of vinylphosphonic acid dichloride were added dropwise over the course of two hours with cooling at 20 ° C. with vigorous stirring. The mixture was then stirred for a further 15 hours and the triethylamine hydrochloride which had formed was subsequently filtered off with suction. The filtrate was washed with tetrahydrofuran, and then was freed from tetrahydrofuran by vacuum distillation. The residue was distilled over a thin-film evaporator at 67 Pa and a bath temperature of 240° C. 345 g, m.p. 70° to 75° C., were obtained. The boiling point was determined by a distillation experiment: 213° to 215° C./53 Pa. The product was produced as a diastereomer mixture. The yield was 90% of theory.

C$_7$H$_{13}$O$_4$P (192): calc.: 43.75% C, 6.77% H, 16.15% P, found: 43.6 % C, 6.8 % H, 16.1 % P.

Example 2 (Compound 2)

Reaction of vinylphosphonic acid dichloride with 1,1,1-trishydroxymethylpropane.

280 g (2.09 mol) of 1,1,1-trishydroxymethylpropane and 422 g (4.18 mol) of triethylamine were dissolved in 1,600 ml of tetrahydrofuran. 303 g (2.09 mol) of vinylphosphonic acid dichloride were then added dropwise over the course of 3 hours with cooling at 20° C. with vigorous stirring. The mixture was stirred for a further 15 hours and the triethylamine hydrochloride which had formed was subsequently filtered off with suction. The filtrate was washed with tetrahydrofuran, and then was freed from the tetrahydrofuran by vacuum distillation. The residue was distilled over a thin-film evaporator at 27 Pa and a bath temperature of 240° C. 370 g were obtained, and the product had a solidification point of about 25° C. The boiling point was determined by a distillation experiment:

199° C./13 Pa. n$_D^{20}$=1.4890.

The product was produced as a diastereomer mixture. The yield was 86% of theory.

C$_8$H$_{15}$O$_4$P (206): calc.: 46.60% C, 7.28% H, 15.05% P, found: 46.4 % C, 7.3 % H, 14.8% P.

Example 3 (Compound 7)

Reaction of methylvinylphosphinic acid chloride with 1,1,1-trishydroxymethylpropane in the ratio 3:1.

20 g (0.15 mol) of 1,1,1-trishydroxymethylpropane and 45.5 g (0.45 mol) of triethylamine were introduced in 150 ml of toluene. 56 g (0.45 mol) of methylvinylphosphinic acid chloride were added dropwise with cooling at 20° C. with vigorous stirring. The mixture was then stirred for a further 15 hours and the triethylamine hydrochloride which had formed was subsequently filtered off by suction. The filtrate was washed with toluene, and then was freed from toluene by vacuum distillation. 58 g of the product having a refractive index n$_D^{20}$=1.4942 remained.

The product could be distilled over a thin-film evaporator at 27 Pa and a bath temperature of 260° to 270° C. The yield of crude product was 97% of theory.

C$_{15}$H$_{29}$O$_6$P$_3$ (398): calc.: 23.37% P, found: 23.1 % P.

Example 4 (Compound 4)

Reaction of methylvinylphosphinic acid chloride with compound 2.

76 g (0.34 mol) of compound 2 were combined with 34.5 g (0.34 mol) of triethylamine in 100 ml of tetrahydrofuran. 42.5 g (0.34 mol) of methylvinylphosphinic acid chloride were then added dropwise with vigorous stirring and cooling at 20° C. The mixture was then stirred for a further 15 hours and the triethylamine hydrochloride which had formed was subsequently filtered off with suction. The filtrate was washed with tetrahydrofuran, and then was freed from tetrahydrofuran by vacuum distillation. 95 g of compound 4 remained. The boiling point was determined by a distillation experiment: 205° to 210° C./67 Pa. The yield of crude product was 95% of theory.

C$_{11}$H$_{20}$O$_5$P$_2$ (294): calc.: 21.09% P, found: 20.5 % P.

Example 5 (Compound 5)

Reaction of ethyl vinylphosphonic acid chloride with compound 2.

34.7 g (0.168 mol) of compound 2 and 17 g (0.168 mol) of triethylamine were introduced into 100 ml of toluene. 26 g (0.168 mol) of ethyl vinylphosphonic acid chloride were then added dropwise with stirring and cooling at 20° C. Stirring was continued, and the mixture was filtered with suction. After washing with toluene, the filtrate was freed from solvent in vacuo. 52.5 g of compound 5, n$_D^{20}$=1.4848 remained.

The product could be distilled in a thin-film evaporator at 27 Pa and a bath temperature of 240° C. The yield of crude product was 96% of theory.

C$_{12}$H$_{22}$O$_6$P$_2$ (324): calc.: 19.13% P, found: 18.7 % P.

Example 6 (Compound 9)

Reaction of vinylphosphonic acid dichloride with compound 2.

82.4 g (0.4 mol) of compound 2 and 40.4 g (0.4 mol) of triethylamine were introduced into 100 ml of toluene. 29 g (0.2 mol) of vinylphosphonic acid dichloride were then added dropwise with stirring and cooling at 20° C. Stirring was continued, the mixture was filtered with suction, and the solid was washed with toluene. The filtrate was freed from toluene in vacuo. 97 g of product having the refractive index $n_D^{20} = 1.4945$ remained.

This corresponds to a yield of 100% of theory.

$C_{18}H_{31}O_9P_3$ (484): calc.: 19.21% P, found: 19.2% P.

Example 7 (Compound 3)

Reaction of vinylphosphonic anhydride with compound 2.

321.4 g (1.56 mol) of compound 2 were dissolved in 321.4 g of methylene chloride. 280.8 g (1.56 mol) of a 50% strength solution of vinylphosphonic anhydride in methylene chloride were then added dropwise over the course of 1 hour with stirring. During this addition, the temperature increased to 33° C. and remained at this temperature for 30 minutes. The mixture was then stirred for a further three hours and subsequently refluxed for a further 4 hours. The solvent was subsequently removed by vacuum distillation over the course of about 3 hours to an internal temperature of 50° C. 130 g of a crude product having the refractive index $n_D^{20} = 1.4945$ remained. On the basis of a $^{31}P$ NMR spectrum, the product was a mixture of two diastereomers, which made up about 60% of the crude product ($d_6$DMSO; $\delta = 14.79$; 14.82; 11.78; 12.73 ppm). The crude product contained 8% of compound 2, 9% of vinylphosphonic acid and 4% of vinylpyrophosphonic acid.

$C_{10}H_{18}O_6P_2$ (296):

Example 8 (Compound 2)

Esterification of vinylphosphonic acid using 1,1,1-trishydroxymethylpropane 53.7 g (0.4 mol) of 1,1,1-trishydroxymethylpropane and 43.2 g (0.4 mol) of vinylphosphonic acid were heated to 160° to 170° C. with stirring at 67 to 133 Pa. As the vacuum was reduced, water collected in a cold trap downstream of the reaction apparatus. When about 7.5 g of water had collected, the reaction temperature was increased to 200° C. with the vacuum improved again, and kept at this temperature for 1 hour. The reaction material produced then had the acid number 134. The mixture was subsequently distilled in a thin-film evaporator at 67 to 133 Pa and a bath temperature of 270° C. The product produced had the acid number 38 and a content of 76% of compound 2, on the basis of the $^{31}P$ NMR spectrum.

Example 9 (Compound 7)

Esterification of methylvinylphosphinic acid using 1,1,1-trishydroxymethylpropane.

33.6 g (0.25 mol) of 1,1,1-trishydroxymethylpropane and 79.5 g (0.75 mol) of methylvinylphosphinic acid were heated in steps over the course of several hours to 190° to 195° C. at 67 to 133 pa with vigorous stirring. 12 g of water collected in a cold trap downstream of the reaction apparatus. The reaction product produced had the acid number 104. The product was distilled in a thin-film evaporator at 260° to 270° C. and 133 Pa. 81 g of product having a content of about 70% of compound 7, on the basis of the $^{31}P$ NMR spectrum, were obtained.

Example 10 (Compound 7)

Transesterification of ethyl methylvinylphosphinate using 1,1,1-trishydroxymethylpropane.

23.5 g (0.175 mol) of 1,1,1-trishydroxymethylpropane, 70.4 g (0.525 mol) of ethyl methylvinylphosphinate and 2.3 g of tetraisopropyl orthotitanate were heated in steps over the course of several hours with vigorous stirring to 210° C. From about 180° C., ethanol distilled off. In total, 12 g of ethanol were collected. The crude product produced had the acid number 75. It could be distilled in a thin-film evaporator at 53 Pa and a bath temperature of 250° to 260° C.

Example 11 (Compound 10)

Reaction of vinylphosphonic acid dichloride with 2,2-bishydroxymethyl-1,3-propanediol.

68.1 g (0.5 mol) of 2,2-bis-hydroxymethyl-1,3-propanediol were introduced into 400 ml of acetonitrile, and 202.4 g (2.0 mol) of triethylamine were added dropwise with stirring. 145 g (1 mol) of vinyldichlorophosphonic acid were added dropwise at 30° C., and the mixture was subsequently stirred for a further 15 hours. The mixture was then heated to reflux and, after about 15 minutes, filtered with suction while hot; crystals again precipitated out of the filtrate and were likewise filtered off with suction. In total, about 265 g of triethylamine hydrochloride were obtained. The acetonitrile was then removed from the filtrate by distillation, and the residue was digested with acetone. 125 g of crude product were obtained. This was recrystallized from isopropanol.

m.p.: 161° C. The yield of crude product was about 90% of theory.

$C_9H_{14}O_6P_2$ (280): calc.: 38.57% C, 5.0% H, 22.14% P, found: 38.3% C, 4.8% H, 21.0% P.

Example 12 (Compound 11)

Esterification of methylvinylphosphinic acid using 2,2-bis-hydroxymethyl-1,3-propanediol.

13.6 g (0.1 mol) of 2,2-bis-hydroxymethyl-1,3-propanediol (pentaerythritol) and 42.4 g (0.4 mol) of methylvinylphosphinic acid were heated in steps over the course of about 5 hours from 155° to 190° C. at about 67 Pa with vigorous stirring. About 6 g of water collected in a cold trap downstream of the reaction apparatus. The crude product produced had the acid number 115. The refractive index was $n_D^{20} = 1.4911$.

$C_{17}H_{32}O_8P_4$ (488): calc.: 25.41% P, found: 25.2% P.

USE EXAMPLES

Example 13

145.5 g of an internally plasticized vinyl alcohol copolymer having a viscosity of 4 mPas in 4% strength aqueous solution at 20° C. and the ester number 150 were dissolved in 147 g of water at 90° C. by stirring. After the mixture had been cooled to 70° C., 100 g of compound 4 (Example 4), 5 g of benzil dimethyl ketal and 1 g of 2,6-di-tert.butyl-4-methylphenol were stirred in. The homogeneous solution was applied in the form of a coating onto a 0.125 mm thick polyethylene terephthalate foil in a manner such that a non-tacky, photosensitive layer of approximate thickness 1 mm resulted after drying for 48 hours at room temperature. A 0.3 mm thick aluminum sheet provided with a polyurethane adhesive coating as in DE-A No. 1,597,515 was placed on the free layer surface, and the multi-layered element was pressed for two minutes in a sheet press at 100° C. The adhesive coating was obtained by reacting a branched polyester made from adipic acid, glycerol and butylene glycol and having an OH group content of 5.2% with triphenylmethane 4,4',4''-triisocyanate. The thickness of the spacers was selected so that a 0.6 mm thick photopolymer coating was obtained after hot pressing. After the polyester film had been removed, the photosensitive coating was exposed imagewise for 10 minutes with a commercially available UVA flat exposer (emission wavelength range 320 to 400 nm, intensity 10 mW/cm$^2$). After the unexposed image areas had been washed out using warm water, a letterpress plate with a good relief structure and a Shore A hardness of 90 was obtained.

Example 14

90 g of a styrene-isoprene-styrene three-block copolymer with a styrene content of 15% (Cariflex TR 1107 from Shell), 10 g of compound 5, 2 g of benzil dimethyl ketal and 0.5 g of 2,6-di-tert.butyl-4-methylphenol were dissolved in 100 g of toluene and cast on a 0.125 mm thick polyethylene terephthalate film to form a 6 mm thick layer. After evaporation of the toluene, a 0.125 mm thick polyethylene terephthalate film provided with an adhesive coating was placed on the free surface of the 3 mm thick photopolymer layer, and the multilayered element was pressed in a sheet press at 100° C. for 10 minutes using 2.8 mm thick spacers. After the uncoated polyester film had been peeled off, the photopolymer layer was exposed for 5 minutes with a commercially available UVA flat exposer (emission wavelength range 320 to 400 nm, intensity 10 mW/cm$^2$) without a mask through the remaining polyester film and for 30 minutes imagewise from the free layer side. After the unexposed image areas had been washed out using tetrachloroethylene, an elastic letterpress plate with a good relief structure (relief depth 1.3 mm) and a Shore A hardness of 55 was obtained.

Example 15

The preparation of the photopolymer layer and the subsequent processing to form a letterpress plate was carried out analogously to Example 13, but in this case 100 g of compound 7 were employed as the crosslinkable monomer. A letterpress plate having a good relief structure and a Shore-A hardness of 98 was obtained.

Example 16

The preparation of the photopolymer layer and the subsequent processing to form a letterpress plate were carried out analogously to Example 13, but in this case 100 g of compound 9 were employed as the crosslinkable monomer. A letterpress plate having a good relief structure and a Shore-A hardness of 95 was obtained.

Example 17

The preparation of the photopolymer layer and the subsequent processing to form a letterpress plate were carried out analogously to Example 13, but in this case 145.5 g of the vinyl alcohol copolymer, 44.6 g of compound 10, 3.9 g of benzil dimethyl ketal and 0.8 g of 2,6-di-tert.butyl-4-methylphenol were processed to form a photopolymer layer. A letterpress plate having a good relief structure and a Shore-A hardness of 98 was obtained.

What is claimed is:

1. A radiation-polymerizable mixture which comprises:
   (a) a polymeric binder,
   (b) a compound which is polymerizable by means of free radicals, and
   (c) a compound which is capable of initiating polymerization of compound (b) under the action of actinic radiation,
   wherein said polymerizable compound is a compound of the formula I

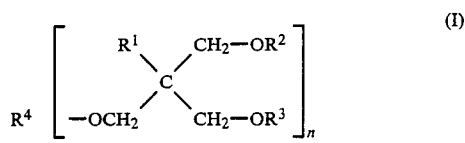

in which
   $R^1$ denotes an alkyl group having 1 to 4 carbon atoms, CH$_2$OH or CH$_2$OR$^7$,
   $R^2$ denotes a group of formula II

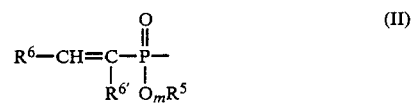

and
   $R^3$ denotes hydrogen atom or a group of the formula II, or in which
   $R^2$ and $R^3$ together denote a group of the formula III

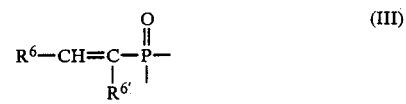

n denotes 1 or 2,
   $R^4$, in the case where n=1, denotes a hydrogen atom, a group of the formula II, or, if $R^2$ and $R^3$ form a group of the formula III and $R^1$ is an alkyl group, denotes a group of the formula IV

or, together with $R^7$, denotes a group of the formula III, and, in the case where n=2, denotes a group of the formula III,
   $R^5$ denotes an alkyl group having 1 to 4 carbon atoms,
   $R^6$ and $R^{6'}$ are identical or different and each denotes a hydrogen atom or an alkyl group having 1 to 4 carbon atoms,
   $R^7$ is a group of the formula II, and
   m is 0 or 1.

2. A radiation-polymerizable mixture as claimed in claim 1, wherein said binder (a) is soluble in water, or soluble or at least swellable in aqueous-alkaline solutions.

3. A radiation-polymerizable mixture as claimed in claim 1, wherein said polymerization initiator (c) is sensitive to visible or long-wave ultra-violet light.

4. A radiation-polymerizable mixture as claimed in claim I, which comprises about 20 to 95% by weight of polymeric binder (a), about 5 to 80% by weight of polymerizable compound (b) and about 0.01 to 10% by weight of polymerization initiator (c).

5. A radiation-polymerization recording material comprising a radiation-sensitive layer which comprises a mixture as claimed in claim 1.

6. A recording material as claimed in claim 5, further comprising a layer support.

7. A recording material as claimed in claim 6, wherein said support has a surface comprising aluminum, steel, zinc or copper.

8. A recording material as claimed in claim 6, wherein said support has a surface comprising a plastic.

9. A recording material as claimed in claim 5, further comprising an oxygen-impermeable film.

* * * * *